United States Patent [19]

Omura

[11] Patent Number: 4,703,758

[45] Date of Patent: Nov. 3, 1987

[54] NON-INVASIVE MONITORING OF BLOOD FLOW AND CEREBRAL BLOOD PRESSURE USING ULTRA MINIATURE REFLECTION TYPE PHOTOELECTRIC PLETHYSMOGRAPHIC SENSORS OR ULTRASONIC DOPPLER FLOW METER

[76] Inventor: Yoshiaki Omura, Apt. 8-I, 800 Riverside Dr., New York, N.Y. 10032

[21] Appl. No.: 705,847

[22] Filed: Feb. 26, 1985

Related U.S. Application Data

[63] Continuation of Ser. No. 429,344, Sep. 30, 1982, abandoned.

[51] Int. Cl.$^4$ .............................................. A61B 5/02
[52] U.S. Cl. ...................................... 128/672; 128/691
[58] Field of Search ............... 128/672, 687, 688, 691, 128/686

[56] References Cited

U.S. PATENT DOCUMENTS

| | | | |
|---|---|---|---|
| 2,249,320 | 7/1941 | McGettee | 128/686 |
| 3,040,737 | 6/1962 | Kompelien et al. | 128/2 |
| 3,167,658 | 3/1965 | Richter | 128/2 |
| 3,228,391 | 1/1966 | Fitter et al. | 128/2 |
| 3,313,945 | 12/1967 | Clinton | 128/2 |
| 3,361,128 | 12/1967 | Colman | 128/2 |
| 3,592,057 | 7/1971 | Boe et al. | 128/2 |
| 3,602,213 | 9/1971 | Howell et al. | 128/2 |
| 3,765,405 | 10/1973 | Natkanski | 128/686 |
| 4,249,540 | 2/1981 | Koyama et al. | 128/691 X |
| 4,332,258 | 6/1982 | Arai et al. | 128/687 X |
| 4,353,374 | 10/1982 | Rebbe et al. | 128/686 |
| 4,354,503 | 10/1982 | Golden | 128/686 |

FOREIGN PATENT DOCUMENTS

| | | | |
|---|---|---|---|
| 2823769 | 12/1979 | Fed. Rep. of Germany | 128/691 |
| 3100610 | 7/1982 | Fed. Rep. of Germany | 128/672 |
| 705933 | 5/1966 | Italy | 128/677 |

OTHER PUBLICATIONS

Omura, Y. "Patho-Physiology of Acupuncture Treatment: Effects of Acupuncture on Cardiovascular and Nervous Systems", Omura,—Hypertension—Part 1: Lower Extremity Hypertension Syndrome and Electro-Acupuncture.

Omura, Yoshiaki et al., "Applications of Ultra-Miniature Photoelectric Plethysmographic Sensors with a Very Short Response Time to the Non-Traumatic Study of the Circulatory System.

Primary Examiner—Edward M. Coven
Attorney, Agent, or Firm—Morgan & Finnegan

[57] ABSTRACT

A device for non-invasively monitoring blood flow comprising a support member having a base surface for engaging the skin, and a light source and a light detector which are supported by the support member above the base surface thereof. The light source emits a beam of light in the form of a cone of relatively small angle, and the light detector receives light directed there towards within a collection cone of relatively large angle. The axis of the light beam crosses the axis of the collection cone below the base surface.

9 Claims, 8 Drawing Figures

NON-INVASIVE MONITORING OF BLOOD FLOW AND CEREBRAL BLOOD PRESSURE USING ULTRA MINIATURE REFLECTION TYPE PHOTOELECTRIC PLETHYSMOGRAPHIC SENSORS OR ULTRASONIC DOPPLER FLOW METER

This is a continuation of co-pending application Ser. No. 429,344 filed on Sept. 30, 1982, now abandoned.

This invention relates to non-invasive monitoring of blood flow, and more particularly to a photoelectric plethysmographic sensor.

The most widely used photoelectric plethysmographic method employs a transmission type sensor comprising a light source and a light detector. The two components of the sensor are placed on opposite sides of a part of the body, for example a finger or earlobe, and light from the light source which is transmitted through the finger, for example, is detected by the detector. The intensity of the light that is transmitted depends upon the blood flow in the path of the light: the more rapid the flow, the lower is the intensity of the transmitted light. Unfortunately, the output intensity of the light source which is needed in order for the blood flow to have a detectable effect upon the intensity of the transmitted light is very high, and this increases the temperature of the skin and consequently the circulatory state of the area of the body where the entering light is distorted. Accordingly, the transmission type PEPG sensor does not provide an accurate indication of the blood flow obtained prior to use of the sensor. Moreover, measurements taken using a transmission type sensor on a finger are inaccurate because the circulation patterns and the distribution of capillary networks and arterioles are quite different on the two sides of the finger.

According to one aspect of the present invention there is provided a device for non-invasively monitoring blood flow, comprising a support member having a base surface for engaging the skin, a light source for producing a beam of light in the form of a cone of relatively small angle, and a light detector for receiving light directed towards the detector within a collection cone of relatively large angle, the light source and the light detector being supported by the support member above the base surface thereof with the axis of the light beam crossing the axis of the collection cone below the base surface.

According to another aspect of the present invention there is provided a non-invasive method of monitoring blood flow in various parts of the body, comprising directing a light beam towards the skin covering a region of the body under investigation at an angle that is oblique to the surface of the skin, collecting light of the beam that is reflected from an interface which lies below said surface and substantially parallel thereto and leaves the body through the skin at an angle that is oblique to the skin, and forming an electrical signal dependent upon the intensity of the light that is reflected.

For a better understanding of the invention, and to show how the same may be carried into effect, reference will now be made, by way of example, to the accompanying drawing in which.

Figure 1:
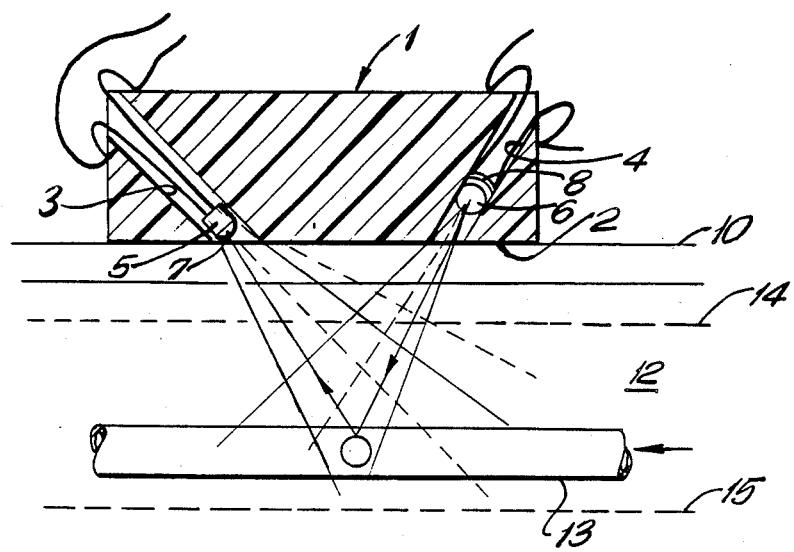
FIG. 1 shows diagrammatically a sectional view of a device embodying the invention, and also illustrates its mode of operation.
Figure 2:
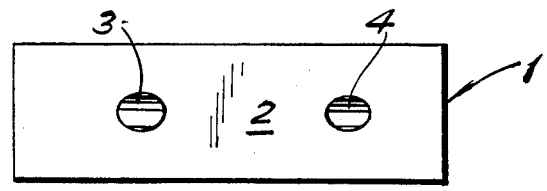
FIG. 2 shows an underneath plan view of the device.

The device illustrated in the drawings comprises a support body 1 having a flat base surface 2 from which two holes 3 and 4 are drilled into the interior of the body, the holes 3 and 4 being inclined with respect to the flat base surface 2 so that the holes diverge from one another as they enter the support body. A phototransistor 5 is received in the hole 3, and a light source 6 is received in the hole 4. The enclosure of the phototransistor 5 includes a lens 7, so that the phototransistor is capable of receiving light directed towards it within a collection cone of relatively large angle for example a half-angle of 30° to 60°, preferably substantially over 40°. The phototransistor is so disposed in the hole 3 as to receive light directed into the hole from beyond the base surface 2. A reflector 8 is positioned in the hole 4 behind the light source 6 so as to reflect light from the source out of the hole 4, past the base surface 2. The light source is positioned quite deeply within the hole 4, so that in combination with the reflector 7 it produces an output light beam in the form of a cone of relatively small angle, for example a half-angle of 15° to 30°. The axis of the collection cone of the phototransistor 5 crosses the axis of the output light beam of the source 6 at a position spaced slightly from the base surface on the opposite side of the base surface from the phototransistor and light source. The expression that the axes cross is not intended to be limited to the axes actually intersecting, but requires only that at least part of the light beam passes through at least part of the collection cone.

Figure 3:
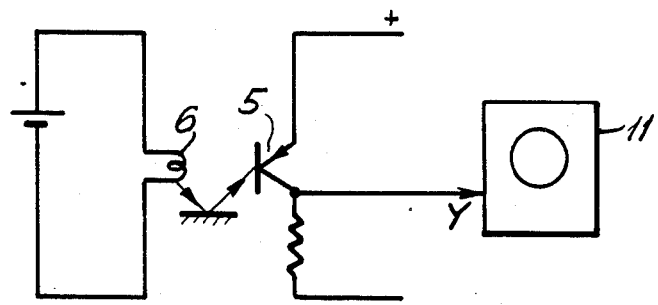
FIG. 3 is a circuit diagram.

When the device is in use, the support body is placed with the base surface 2 in contact with the patient's skin 10, and the light source 6 is energized and the collector electrode of the phototransistor 5 is connected to the Y input of an oscilloscope 11, as illustrated in FIG. 3.

Light from the light source 6 penetrates the skin and the subcutaneous tissue 12. If the device is placed immediately above a blood vessel 13, light is reflected from the blood cells flowing in the blood vessel. Of course, the light that is reflected from the blood in the vessel 13 will not be reflected as if the vessel were in fact a continuous member of reflective material, but some of the light will be reflected towards the phototransistor, resulting in an increased output voltage signal therefrom. The intensity with which the light is reflected is directly dependent upon the rate of flow of blood along the vessel 13. The reason for this is that when the blood flows rapidly, the cells present an almost continuous reflective surface to the light beam, whereas when the blood flows slowly the interstices between the cells allow light to pass through the vessel deeper into the patient's body and to be absorbed therein. As the rate of blood flow varies, so also varies the collector voltage of the phototransistor.

It will be apparent from FIG. 1 of the drawing that in order for light of the output light beam from the source 6 to be reflected into the collection cone of the phototransistor 5, the reflective surface must be located between the levels denoted 14 and 15 in FIG. 1. The distance between the levels 14 and 15 is sufficiently small for there to be relatively few blood vessels between these levels, and accordingly the accuracy of the output voltage of the phototransistor, as a measure of the rate of blood flow through the vessel 13, will not be impaired by the effect of light transmitted from other blood vessels. Moreover, the device is very small, being only about 6~10 mm long by 3~5 mm wide, and experiments show that it is possible using this device to monitor the rate of blood flow in a single blood vessel.

Figure 4:
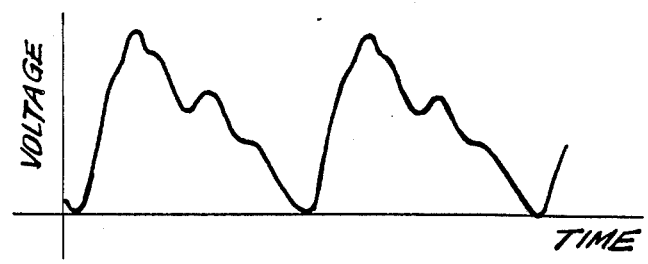
FIG. 4 is a graph of voltage against time.
Figure 5:
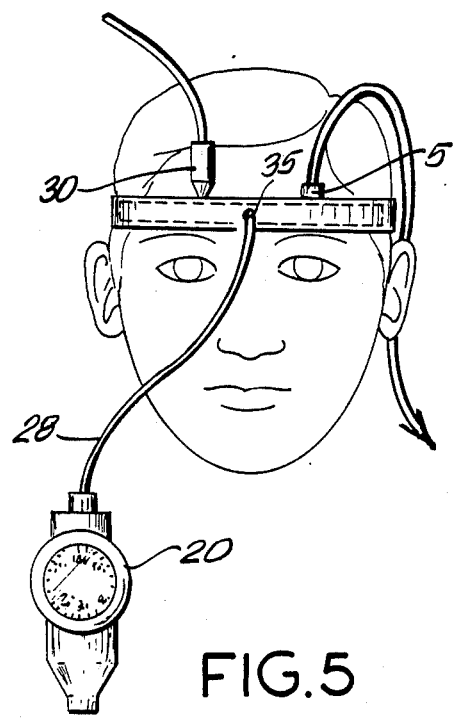
FIG. 5 shows the present invention in use on the forehead to measure supraorbital arterial blood pressure.

Experiments have been carried out using the illustrated device to measure the blood flow in the supra-orbital artery. (The supra-orbital artery flows upwardly from the eye socket over the forehead.) It is found that the output voltage wave form corresponds very closely to the variation in blood pressure (although, strictly speaking, intensity of reflected light depends upon the blood flow, not upon the blood pressure), as illustrated in FIG. 4, having the characteristic systolic up-slope, systolic down-slope, dicrotic notch, dirotic peak and diastolic down-slope. By trying a blood-pressure cuff around the patient's head, so that it passes over the supra-orbital artery between the eye socket and the position of the device, the pulsating form of the variation in blood flow is supressed and the output voltage of the phototransistor 5 is then a measure of the patient's systolic blood pressure.

The phototransistor that is actually used is type manufactured by Texas Inst. or others. The light source is an incandescent pin light approximately 1 mm or less in diameter such as manufactured by Pin Lite Co. of New Jersey. Instead of a phototransistor, a photodiode could be used. The reflector 7 is made of aluminum foil and serves not only as a reflector but also as a heat sink to dissipate the heat generated by the incandescent light source 6.

Approximate blood pressure of the brain and the eyes can also be estimated, by measuring the supraorbital (or supratrochlear) arterial blood pressure using reflection photoelectric plethysmographic sensors with combination of special head band type blood pressure cuff specially designed for this purpose.

Figure 6:
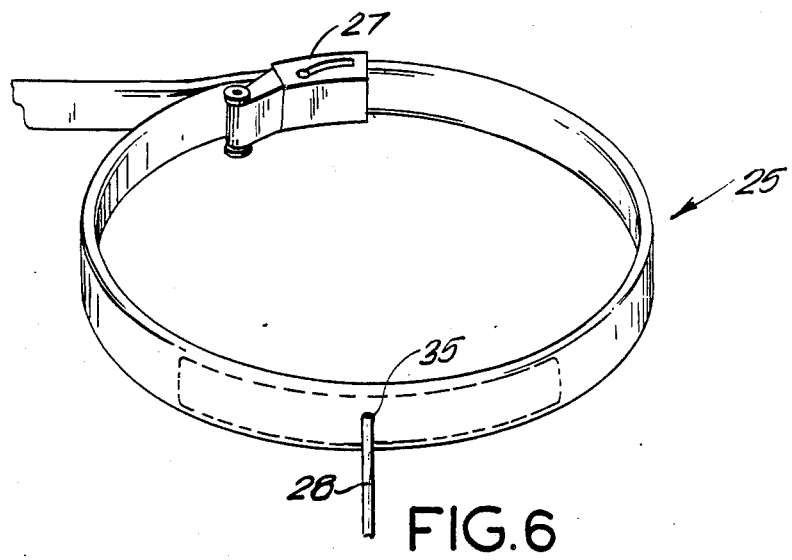
FIG. 6 shows a head band blood pressure cuff which is a part of the present invention.
Figure 7:
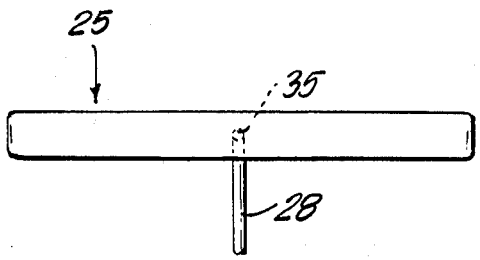
FIG. 7 shows a first embodiment of the head band blood pressure cuff shown in FIG. 6.
Figure 8:
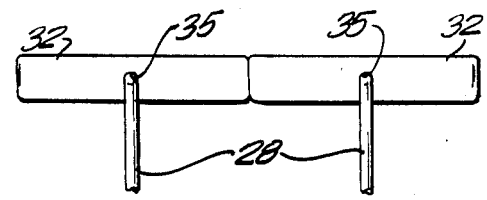
FIG. 8 shows a second embodiment of the head band blood pressure cuff shown in FIG. 6.

The most important part of this supraorbital arterial blood pressure measurement consists of a blood pressure cuff head band made like a slide control buckle system belt, with a specially designed inflatable cuff having a width of approximately 2 cm for adults and somewhere between 1.5 and 2 cm for children. The length of the cuff should sufficiently cover the entire forehead. The center of the cuff has a rubber tube stuck through a hole in the belt and which is to be connected to the blood pressure manometer. This supraorbital head band encircles the head and the inflatable cuff is held against the forehead by tightening the belt. The head band pressure cuff can be divided into 2 compartments with separate tubing for each, for special study (FIGS. 6 & 8).

It will be appreciated that the invention is not limited to the particular device described and illustrated, since modifications may be made without departing from the scope of the invention as defined in the appended claims.

What is claimed is:

1. An apparatus located outside a patient's skull for diagnosing cephalic hypertension or cephalic hypotension and retinal and cerebral circulatory disturbances within a patient'skull,
   comprising:
   cerebral and retinal monitoring means for non-invasively monitoring from outside of the patient's skull blood pressure and flow of a supra-orbital artery and a supra-trochlear artery, said monitoring means including either a support member having a base surface for engaging the skin, a light source for producing a beam of light in the form of a cone of relatively small angle, and a light detector for receiving a light directed towards the detector within a collection cone of relatively large angle, the light source and the light detector being supported by the support member above the base surface thereof with the axis of the light beam crossing the axis of the collection cone below the base surface, to measure supra-orbital and supra-trochlear arterial blood pressure and flow, and
   means for suppressing blood flow through the supra-orbital artery and the supra-trochlear artery, said suppressing means including
   a head band having at least a partially inflatable cuff for contacting a forehead to suppress blood flow in the supra-orbital artery and the supra-trochlear artery during blood pressure measurement, the cuff having critical dimensions of a length sufficient to cover the forehead and of a width of substantially between 1.5 to 2.0 cm depending upon the size of the forehead to ensure sensitive, accurate measurement of blood flow through the supra-orbital artery and the supratrochlear artery, the device being for indicating when blood has been suppressed, and means for measuring the pressure in the cuff needed to stop blood flow.

2. An apparatus as claimed in claim 1, wherein the half-angle of the cone of the light beam is substantially 15° to 30°.

3. An apparatus as claimed in claim 1, wherein the half-angle of the collection cone of the detector is substantially 30° to substantially 60°.

4. An apparatus as claimed in claim 1, wherein the light detector is a phototransistor provided with a convex lens.

5. An apparatus as claimed in claim 1, wherein the light source is an incandescent light source and is provided with a metallic heat sink in the form of a reflector.

6. An apparatus as claimed in claim 1 in which the cuff includes at least one inflatable compartment.

7. An apparatus according to claim 1 wherein said monitoring means includes an ultrasonic doppler flow meter to measure supra-orbital and supra-trochlear arterial blood pressure and flow.

8. An apparatus according to claim 7 wherein said ultrasonic doppler flow meter has an operating frequency of 8 MHZ.

9. A non invasive method of diagnosing cephalic hypertension or cephalic hypotension and retinal and cerebral circulatory disturbances within a patient's skull without opening a patient's skull from outside a patient's skull, the steps comprising:
   non-invasively monitoring from outside of a patient's skull cerebral blood pressure and flow of a supraorbital artery and a supra-trochlear artery by means of cerebral and retinal monitoring means; and
   suppressing blood flow through the supra-orbital artery and the supra-trochlear artery by suppressing means to ensure sensitive, accurate measurement of blood flow through the supraorbital artery and the supra-trochlear artery by said monitoring means thereby obtaining accurate blood pressure measurements of said supra-orbital and said supra-trochlear arteries to diagnose cephalic hypertension or cephalic hypotension and retinal and cerebral circulatory disturbances of the patient.

* * * * *